United States Patent [19]

Wen et al.

[11] 4,161,518
[45] Jul. 17, 1979

[54] COMPOSITIONS AND METHODS FOR INHIBITING PLAQUE FORMATION

[75] Inventors: Richard Y. Wen, New Brighton; Linda L. LaFleur, Oakdale; Michael R. Engel, White Bear Lake; Anthony J. Lucas, Afton, all of Minn.

[73] Assignee: Minnesota Mining and Manufacturing Company, St. Paul, Minn.

[21] Appl. No.: 865,707

[22] Filed: Dec. 29, 1977

[51] Int. Cl.$^2$ ............................ A61K 7/18; A61K 7/22
[52] U.S. Cl. ............................................ 424/52; 424/54
[58] Field of Search .................................... 424/48-58, 424/184

[56] References Cited

U.S. PATENT DOCUMENTS

| | | | |
|---|---|---|---|
| 2,580,473 | 1/1952 | Sowa et al. | 424/184 X |
| 2,806,814 | 9/1957 | Richter | 424/48 |
| 2,921,885 | 1/1960 | Bouchal | 424/54 |
| 3,124,512 | 3/1964 | Schmid et al. | 424/52 |
| 3,297,452 | 1/1967 | Wing et al. | 424/48 X |
| 3,507,955 | 4/1970 | Osipow | 424/54 |
| 3,624,120 | 11/1971 | Yetter | 424/184 X |
| 3,703,583 | 11/1972 | Martin | 424/54 |

OTHER PUBLICATIONS

Iler Chem. Abstracts 50:5313c (1956) of U.S. Pat. No. 2,721,812; Oct. 25, 1955; "Quaternary Ammonium Organo Siloxanolates and their Applications," (Dispersing and Emulsifying Agents Showing Marked Surface Activity).

Morehouse Chem. Abstracts 55:13315c (1961) of U.S. Pat. No. 2,972,598, Feb. 21, 1961.

A.D.A. Accepted Dental Therapeutics 35th Ed. (1973), pp. 55:Silicone Fluids, 60-64 Quat. Amm. Cpds.; 193-194 Quat. Amm. Cpds.; 253-258:Dentrifrices and Mouthwashes; 264≧266, Detergents–Surface Active Agents.

*Primary Examiner*—Shep K. Rose
*Attorney, Agent, or Firm*—C. Alexander; D. M. Sell; J. V. Lilly

[57] ABSTRACT

A dentifrice composition is provided containing a quaternary ammonium organosiloxane having the formula

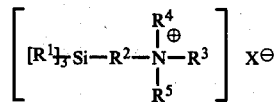

wherein $R^1$ is an alkoxy group having from 1 to 5 carbon atoms, $R^2$ is an alkylene group having from 1 to 25 carbon atoms, and $R^3$, $R^4$ and $R^5$ are, individually, alkyl groups of from 1 to 25 carbon atoms, and X is an anion, preferably selected from chlorine, bromine fluorine and iodine. A method of inhibiting plaque formation on teeth in an oral environment is also provided.

15 Claims, No Drawings

COMPOSITIONS AND METHODS FOR INHIBITING PLAQUE FORMATION

BACKGROUND OF THE INVENTION

1. Field of the Invention

This invention relates to compositions and methods useful in inhibiting the growth of cariogenic bacteria and the formation of plaque on teeth in an oral environment.

2. Prior Art

The prevention of the formation of dental plaque is a highly desired result. Dental plaque results when cariogenic bacteria (e.g., *Streptococcus Mutans*) collect on colonies on the surface of teeth and form a tenacious deposit thereon. The presence of both the bacteria and the deposits is extremely detrimental to the health of the teeth. Thus, if the cariogenic bacteria and the plaque formation are not checked they may result in infected gingival tissue, the formation of dental caries and periodontal disease. In extreme cases they may ultimately result in the loss of teeth.

To overcome these problems many attempts have been made to control cariogenic bacteria and the formation of plaque on teeth. For example, fluoride solutions or gels have been used. Treatment with these materials is typically performed in a dental office at periodic, but not frequent, intervals. The primary objective of these treatments is to render the tooth enamel more resistant to the acid action caused by plaque. Such treatments do not, however, result in plaque control for an extended period since plaque reestablishes itself on the teeth shortly after ingestion of food.

Even when the frequency of application of such solutions and gels is increased only partial control has been shown. For example, studies wherein a fluoride-containing solution (1% fluoride concentration) was applied four to five times in the course of a year have demonstrated that this technique had only limited success due to the rapid reestablishment of plaque in the oral cavity. Moreover, the daily application of a fluoride gel by means of a custom-fitted polyvinyl mouthpiece for a period of twenty-one months also showed no substantial change in plaque formation among treated and untreated patients. See "Clinical Anticaries Effect of Repeated Topical Sodium Fluoride Application by Mouthpiece", Journal of the American Dental Association, V. 75, No. 3, September, 1967, pp. 638–644.

Other attempts at inhibiting the formation of plaque have also been made. For example, U.S. Pat. No. 3,733,399 describes toothpaste compositions which contain the enzyme invertase as the active ingredient. Another approach is disclosed in U.S. Pat. No. 3,894,147 wherein the application to teeth of a dialkyl pyrophosphate having from about 8 to 14 carbon atoms in the alkyl groups is described as useful in inhibiting plaque formation.

Each of the foregoing approaches require frequent (e.g., daily) use, in order to effectively control the cariogenic bacteria and inhibit the formation of plaque over an extended period of time. The present invention, however, provides compositions which are useful in controlling cariogenic bacteria and inhibiting the formation of plaque over an extended period of time despite relatively infrequent application to teeth.

SUMMARY OF THE INVENTION

In accordance with the present invention there is provided a dentifrice composition which contains a quaternary ammonium organosiloxane having the formula

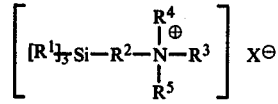

wherein $R^1$ is an alkoxy group having from 1 to 5 carbon atoms, $R^2$ is an alkylene group having from 1 to 25 carbon atoms, and $R^3$, $R^4$ and $R^5$ are, individually, alkyl groups of from 1 to 25 carbon atoms, and X is an anion, preferably selected from chlorine, bromine, fluorine and iodine. Preferably, compositions of the invention contain at least about 0.05% by weight, and most preferably from about 0.25% to 1% by weight, of the quaternary ammonium organosiloxane.

In another embodiment of the present invention there is provided a method for inhibiting plaque formation which comprises contacting teeth with an effective amount of the above-described composition.

As it is used throughout this specification the term "dentifrice" refers to compositions for topical application to the teeth. Representative of such compositions are mouthwashes or rinses, toothpastes, gels, etc.

DETAILED DESCRIPTION OF THE INVENTION

The dentifrice compositions of the invention may be applied to the teeth by a variety of techniques such as painting or brushing, spraying, bathing and rinsing. Other means of application are also possible and will be obvious to those in the art as a result of this disclosure. After application to the teeth it is preferred that the teeth be allowed to dry for a short period of time (e.g., one minute) before the user eats or drinks.

The organosiloxanes useful in the present invention are known materials that may be prepared by simply agitating a warm mixture of an appropriate tertiary amine (e.g.,

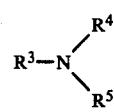

wherein $R^3$, $R^4$ and $R^5$ are as described above) and an appropriate silane (e.g., $[R^1]_3$—Si—$R^2$X wherein $R^1$, $R^2$ and X are as described above).

In the present invention it is preferred that $R^1$ be a methoxy group (i.e., $CH_3O$—), $R^2$ be an alkylene group having 1 to 10 carbon atoms (most preferably a propylene group, i.e., —$CH_2$—$CH_2$—$CH_2$—), $R^3$ be an alkyl group having from 10 to 20 carbon atoms (most preferably an octadecyl group, i.e., —$C_{18}H_{37}$), $R^4$ and $R^5$ each be methyl groups (i.e., $CH_3$—) and X be chlorine. Thus, the most preferred siloxane may be represented by the formula

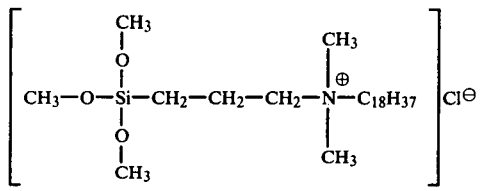

This compound, may also be referred to as 3-(trimethoxysilyl)-propyl-dimethyloctadecyl ammonium chloride. It may be obtained from Dow Corning Corporation as "Q9-5700" as a 50% by weight solution of the siloxane in methanol.

When provided in solution form, dentifrices of the present invention typically comprise a solution of the organosiloxane in water or a mixture of water and an alcohol. Typically the alcohol is a lower, non-toxic alkanol (e.g., ethanol, propanol, etc.). Liquid solutions of the siloxane are particularly useful as mouthwashes or rinses.

A variety of other ingredients may be added to the dentifrices of the present invention. Thus, for example, prophylactic agents may be included. Moreover, polishing agents, soaps or detergents, flavoring and sweetening agents, thickening agents and humectants may be included using techniques which are known to the art. Preferably these other ingredients are free from polyvalent metal ions such as calcium and magnesium.

Representative prophylactic agents include supplemental caries-preventing materials such as sodium fluoride, stannous fluoride, potassium fluoride, hexylamine hydrofluoride, myristylamine hydrofluoride, betaine fluoride, glycine potassium fluoride, etc. A particularly preferred fluoride is sodium fluoride. Typically these prophylactic agents are present in sufficient concentrations so as to provide an available fluoride ion concentration of up to about 2% by weight, and preferably in the range of about 0.5-2% by weight, of the dentifrice composition.

Suitable polishing agents include, for example, abrasive materials such as insoluble condensed phosphates such as calcium pyrophosphate, insoluble calcium polyphosphate (also known as calcium polymetaphosphate) and highly polymerized sodium polyphosphate (also known as sodium polymetaphosphate); and water-impervious cross-linked thermosetting resins such as the condensation products of melamine and urea with formaldehyde. Other suitable polishing agents will be obvious to those skilled in the art as a result of this disclosure.

Preferably the polishing agent is not so abrasive so as to scratch or unduly abrade the tooth surface or the dentin. Rather it only cleans the tooth surface. The polishing agents may comprise up to 95% by weight of the dentifrice composition.

Soaps or detergents may also be employed in the present invention so as to lower the surface tension of the compositions of the invention. Suitable soaps include, for example, the soaps of high molecular weight fatty acids such as sodium and potassium soaps of myristic, stearic palmitic acids and fatty acid mixtures of palm oil and coconut oil. Typical synthetic detergents include alkyl sulfates and sulfonates having alkyl groups of from about 8 to 18 carbon atoms, such as sodium lauryl sulfate, the sulfated fatty alcohols derived from coconut oil and palm oil, etc. The soaps typically comprise up to about 5% by weight of the dentifrice composition.

Suitable flavoring and sweetening agents include, for example, the oils of wintergreen, peppermint, spearmint, sassafras and anise. Additionally small amounts of sweetening agents such as saccharin, dextrose, levulose, etc. may also be added to such compositions. These flavoring and sweetening agents may comprise up to about 5% by weight of the dentifrice composition.

Suitable gelling or thickening agents include, for example, water-soluble salts of cellulose ethers such as sodium carboxymethyl cellulose and sodium carboxy methyl hydroxy ethyl cellulose; natural gums such as gum karaya, gum arabic, and gum tragacanth; and colloidal magnesiumaluminum silicate or finely divided silica. Such thickening agents may comprise up to about 5% by weight of the dentifrice composition.

Suitable humectants which may be employed in compositions of the invention include glycerine, sorbitol, and other polyhydric alcohols. The humectants may comprise up to about 35% by weight of the dentifrice composition.

Tests to demonstrate the effectiveness of the present invention in inhibiting the growth of plaque were performed on Rhesus Monkeys. The teeth of the monkeys were clinically preconditioned to a plaque-free state by ultrasonic cleaning and subsequent dental prophylaxis using a soft rubber prophylaxis cup and standard pumice-filled prophylaxis paste. The teeth were then treated in various fashions and the effect of the treatment upon the formation of plaque was observed.

The effectiveness of plaque inhibition was measured by means of a plaque index number. Plaque index was determined by applying erythrosine B dye, further identified as FD&C Red dye #3, Color Index No. 45430, to the teeth. This dye stains plaque but not tooth enamel. The stained plaque was visually observed and assigned a rating number using the following scale.

| PLAQUE SCALE | |
| --- | --- |
| 0 | No plaque |
| 0.25 | Light plaque covering about ¼ of tooth surface |
| 0.5 | Light plaque covering about ½ of tooth surface |
| 0.75 | Light plaque covering about ¾ of tooth surface |
| 1.0 | Light plaque covering entire tooth surface |
| 1.25 | Heavy plaque on ¼ of tooth surface, light plaque on remainder. |
| 1.50 | Heavy plaque on ½ of tooth surface, light plaque on remainder. |
| 1.75 | Heavy plaque on ¾ of tooth surface, light plaque on remainder. |
| 2.0 | Heavy plaque on entire tooth surface. |

The plaque was observed visually and rated periodically for the duration of the test. The ratings for each monkey were then averaged to obtain a plaque index for each monkey.

A solution containing 3-(trimethoxysilyl)-propyl-dimethyloctadecylammoniumchloride ("Q9-5700") was applied to the upper incisors of the test monkeys. Solution A comprised 50% "Q9-5700" and 50% methanol by weight. Solutions B & C each comprised 1% "Q9-

"5700", 1% methanol and 98% deionized water by weight. Different lots of "Q9-5700" were employed in Solutions B & C. The untreated teeth of the monkeys served as a control. They received no preventative treatment during the tests.

The monkeys were fed twice a day with a diet which encouraged plaque formation. The diet consisted of about 135 grams of Purina® New World Monkey Chow® which had been softened with 200 milliliters of distilled water and to which 118 grams of sugar had been added. The Monkey Chow® is commercially available from Ralston Purina Co. It has a guaranteed analysis of

| Crude protein not less than | 25.0% |
| Crude fat not less than | 5.0% |
| Crude fiber not more than | 3.5% |
| Added minerals not more than | 3.0% |
| Ash not more than | 6.0% |

The ingredients in the Monkey Chow® were ground yellow corn, soybean meal, ground wheat, corn gluten meal, dried skimmed milk, animal fat preserved with BHA, sucrose, brewers' dried yeast, salt, dehydrated alfalfa meal, vitamin $B_{12}$ supplement, riboflavin supplement, calcium pantothenate, niacin, choline chloride, menadione sodium bisulfite (source of vitamin K activity), folic acid, pyridoxine hydrochloride, thiamin, ascorbic acid, vitamin A supplement, D activated animal sterol (source of vitamin $D_3$), vitamin E supplement, iron oxide, iron sulfate, manganese sulfate, calcium iodate, calcium carbonate, dicalcium phosphate, manganous oxide, copper oxide, cobalt carbonate, zinc oxide.

The results of the tests are as set forth in the following table:

| MONKEY # | SOLUTION | TREATMENT | # OF DAYS TEST LENGTH | PLAQUE INDEX TREATED TEETH | CONTROL TEETH |
|---|---|---|---|---|---|
| 1 | A | 1 | 14 | .270 | 1.58 |
| 2 | B | 1 | 14 | .35 | 1.25 |
| 3 | C | 1 | 12 | .50 | 1.00 |
|   | C | 2 | 12 | .187 | 1.312 |
| 4 | C | 3 | 12 | .281 | 1.437 |
| 5 | C | 4 | 12 | .56 | 1.437 |
| 6 | C | 1 | 12 | 1.625 | 1.75 |
|   | C | 5 | 9 | .312 | >2.0 |
| 7 | C | 2 | 9 | .375 | 1.875 |

TREATMENT
1 On day 1 the solution was brushed onto the teeth with a paint brush and air dried for 2 minutes. There was no further treatment for duration of the test.
2 The teeth were brushed daily with the solution.
3 On day 1 the solution was brushed onto the teeth with a paint brush, air dried for 2 minutes. Thereafter the treated teeth were brushed daily with deionized water.
4 On day 1 the solution was brushed onto the teeth with a paint brush, air dried for 2 minutes. Thereafter the treated teeth were brushed daily with a composition of 1% by weight

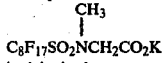

$C_8F_{17}SO_2NCH_2CO_2K$ in deionized water.
5 The teeth were rinsed daily with 1cc of the solution.

Monkey 6 salivated excessively. Hence the single application of Solution C was rinsed away. However, when Solution C was later applied to the same monkey each day for 9 days it provided effective plaque control. Similar plaque control is achieved when the methanol employed in the solutions is removed or is replaced with a non-toxic alcohol such as ethanol.

What is claimed is:

1. A dentifrice composition which consists essentially of at least one ingredient selected from the group consisting of caries prophylactic agents, soaps, detergents, flavoring agents, sweetening agents and humectants and at least about 0.05% by weight of a quaternary ammonium organosiloxane having the formula

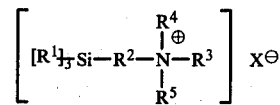

wherein $R^1$ is an alkoxy group having from 1 to 5 carbon atoms, $R^2$ is an alkylene group having from 1 to 25 carbon atoms, and $R^3$, $R^4$ and $R^5$ are, individually, alkyl groups of from 1 to 25 carbon atoms, and X is an anion.

2. A dentifrice composition in accordance with claim 1 wherein X is selected from chlorine, bromine, fluorine and iodine.

3. A dentifrice composition according to claim 2 wherein said composition contains at least about 0.05% to 1% by weight of said quaternary ammonium organosiloxane.

4. A dentifrice composition according to claim 3 wherein $R^1$ is methoxy, $R^2$ is an alkylene group having from 1 to 10 carbon atoms, $R^3$ is an alkyl group having from 10 to 20 carbon atoms, $R^4$ and $R^5$ are, individually, methyl groups, and X is chlorine.

5. A dentifrice composition according to claim 4 wherein $R^2$ is a propylene group and $R^3$ is an octadecyl group.

6. A dentifrice composition according to claim 1 in the form of a paste.

7. A dentifrice composition according to claim 1 in the form of a powder.

8. A dentifrice composition according to claim 1 in the form of a liquid.

9. A method of inhibiting plaque formation by contacting teeth with an effective amount of a dentifrice composition which contains at least about 0.05% by weight of a quaternary ammonium organosiloxane compound having the formula

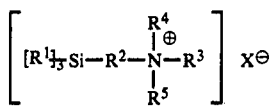

wherein $R^1$ is an alkoxy group having from 1 to 5 carbon atoms, $R^2$ is an alkylene group having from 1 to 25 carbon atoms, and $R^3$, $R^4$ and $R^5$ are, individually, alkyl groups of from 1 to 25 carbon atoms, and X is an anion.

10. The method of claim 9 wherein X is selected from chlorine, bromine, fluorine and iodine.

11. The method of claim 10 wherein $R^1$ is methoxy, $R^2$ is an alkylene group having from 1 to 10 carbon atoms, $R^3$ is an alkyl group having from 10 to 20 carbon atoms, $R^4$ and $R^5$ are, individually, methyl groups, and X is chlorine.

12. The method of claim 11 wherein $R^2$ is a propylene group and $R^3$ is an octadecyl group.

13. The method of claim 9 wherein said teeth are contacted by a composition comprising at least about 0.05% by weight of said quaternary ammonium organosiloxane compound.

14. A dentifrice composition, free of polyvalent metal ions, which composition consists essentially of at least one ingredient selected from the group consisting of caries prophylactic agents, soaps, detergents, flavoring agents, sweetening agents and humectants and at least about 0.05% by weight of a quaternary ammonium organosiloxane having the formula

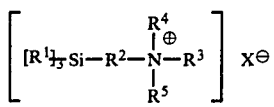

wherein $R^1$ is an alkoxy group having from 1 to 5 carbon atoms, $R^2$ is an alkylene group having from 1 to 25 carbon atoms and $R^3$, $R^4$ and $R^5$ are, individually, alkyl groups of from 1 to 25 carbon atoms, and X is an anion.

15. A dentifrice composition according to claim 1 in the form of a gel.

* * * * *